United States Patent [19]

McLean et al.

[11] Patent Number: 5,393,877

[45] Date of Patent: Feb. 28, 1995

[54] LINKERS FOR THE SYNTHESIS OF MULTIPLE OLIGONUCLEOTIDES IN SERIATIM FROM A SINGLE SUPPORT ATTACHMENT

[75] Inventors: Michael J. McLean, Nantwich; David Holland, Macclesfield; Andrew J. Garman, Ashton; Robert C. Sheppard, Cambridge, all of England

[73] Assignee: Zeneca Limited, London, England

[21] Appl. No.: 41,599

[22] Filed: Apr. 5, 1993

[30] Foreign Application Priority Data

Apr. 3, 1992 [GB] United Kingdom ............... 9207381

[51] Int. Cl.⁶ .............................................. C07H 21/00
[52] U.S. Cl. .................... 536/25.3; 536/25.31; 536/25.33; 536/25.34; 558/199
[58] Field of Search ............... 536/25.3, 25.31, 25.33, 536/25.34; 558/199

[56] References Cited

FOREIGN PATENT DOCUMENTS 0067597 12/1982 European Pat. Off. ............... 435/91
9021625 10/1993 United Kingdom ............... 536/25.3
9206103 4/1992 WIPO ................................. 536/25.3

OTHER PUBLICATIONS

Agarwal et al., "Studies on Polynucleotides. CXLIII. A Rapid and Convenient Method for the Synthesis of Deoxyribooligonucleotides Carrying 5'-Phosphate End Groups Using a New Protecting Group," *J. Am. Chem. Soc.*, 98(5), 1065-1072 (1976).

Brandstetter et al., "Neue Polymer-Schutzgruppe in der Oligonucleotidesyntheses, 2-hydroxyäthylphenylthioäther von Polyäthyleneglykol," *Tett. Lett.*, 1974(31), 2705-2708.

Ikehara et al., "The Synthesis of Polynucleotides," *Adv. Carbohydrate Chem. Biochem.*, 36, 135-213 (1979): only pp. 135 and 204-213 supplied.

*Primary Examiner*—John W. Rollins
*Assistant Examiner*—L. Eric Crane
*Attorney, Agent, or Firm*—Cushman Darby & Cushman

[57] ABSTRACT

A method for the synthesis of a plurality of oligonucleotides comprising the steps of (i) forming a first oligonucleotide on a first cleavable link attached to a solid support;

(ii) attaching to the first oligonucleotide a cleavable linker moiety;

(iii) forming a second oligonucleotide on the cleavable linker moiety; and (iv) cleaving the first cleavable link and the cleavable linker moiety to give a plurality of oligonucleotides; wherein the cleavable linker moiety is of the Formula (1):

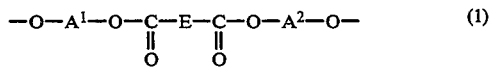

in which $A^1$, $A^2$ and E are as defined herein, and novel compounds which may be used in the operation of the method.

17 Claims, No Drawings

LINKERS FOR THE SYNTHESIS OF MULTIPLE OLIGONUCLEOTIDES IN SERIATIM FROM A SINGLE SUPPORT ATTACHMENT

This invention relates to a method for the synthesis of oligonucleotides and to novel compounds which may be used during operation of the method.

Oligonucleotide sequences are routinely synthesised for use as linkers, adaptors, building blocks for synthetic genes, synthetic regulatory sequences, probes, primers and other purposes and a number of methods have been developed for producing such sequences. These methods rely on the initial attachment of a first suitably protected nucleoside to a solid support by a cleavable linkage followed by sequential reactions of precursors of individual nucleotides to the growing oligonucleotide strand with each addition of a precursor involving a number of chemical reactions. At present the method most generally employed for the production of a lone oligonucleotide is based on phosphoramidite chemistry. This is fully described by Caruthers et al in Tetrahedron Letters 1981, 22, (20) pp 1859–62, by Koster et al in U.S. Pat. No. 4,725,677 and by M. J. Gait ('Oligonucleotide Synthesis, a Practical Approach', IRL Press Oxford p35–81).

Several types of automated DNA synthesisers are now commercially available which enable an oligonucleotide to be prepared using phosphoramidite chemistry. An illustrative description of how a lone oligonucleotide may be formed by sequential reactions of precursors of the individual nucleotides on a support is provided in the protocol for the Applied Biosystems DNA Synthesiser Model 380B, particularly Section 2 thereof, which is incorporated herein by reference thereto.

In response to the rapid increase in demand for oligonucleotides, improvements are desirable which will increase the throughput of commercial synthesisers, i.e. increase the number of oligonucleotides synthesised per day.

We have now developed a rapid and efficient method for the production of oligonucleotides in which more than one oligonucleotide can be synthesised on the same support using a cleavable linker moiety introduced as required in a growing oligonucleotide chain.

According to a first aspect of the present invention there is provided a method for the synthesis of a plurality of oligonucleotides comprising the steps of:

(i) forming a first oligonucleotide on a first cleavable link attached to a solid support;
(ii) attaching to the first oligonucleotide a cleavable linker moiety;
(iii) forming a second oligonucleotide on the cleavable linker moiety; and
(iv) cleaving the first cleavable link and the cleavable linker moiety to give a plurality of oligonucleotides;

wherein the cleavable linker moiety is of the Formula (1):

$$-O-A^1-O-\underset{\underset{O}{\|}}{C}-E-\underset{\underset{O}{\|}}{C}-O-A^2-O- \quad (1)$$

wherein one or both of $A^1$ and $A^2$ is a divalent group of the formula (a):

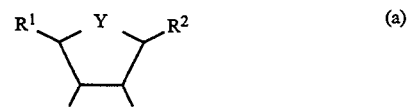

$R^1$ and $R^2$ are each independently H, optionally substituted alkyl, optionally substituted alkoxy or optionally substituted aryloxy, halogen, cyano, nitro, optionally protected hydroxy, optionally protected oxycarbonyl, optionally protected $NH_2$, or an electron withdrawing group; Y is $CH_2$, $CH_2CH_2$, NH, S or O; E is an organic spacer group; and any remaining group represented by $A^1$ or $A^2$ is of the formula (b):

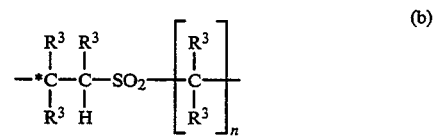

wherein n has a value of from 1 to 5; the carbon atom marked with an asterisk is attached to an oxygen atom shown in Formula (1); and each $R^3$ independently represents H or optionally substituted alkyl.

It is preferred that $A^1$ and $A^2$ are both of Formula (a) and n preferably has a value of from 1 to 3, more preferably 2.

The support is preferably a solid support such as is used in automated oligonucleotide synthesis. The preferred solid support is, for example, a modified inorganic polymer such as those disclosed in the U.S. Pat. No. 4,458,066, a silica gel, Porasil C, kieselguhr PDMA, polystyrene, polyacrylamide, Silica CPG (LCAA) or a controlled pore glass as used in, for example, the Applied Biosystems DNA synthesiser Model 380B. The oligonucleotides may be formed from precursors of individual nucleotides by conventional technology used for synthesising oligonucleotides, for example by using phosphoramidite chemistry on an automated oligonucleotide synthesiser as described above. The first oligonucleotide is preferably connected to the support by a hydrolysable group (e.g. a base labile group) as is known in the art.

The first aspect of the invention may be illustrated by the formation of 2 oligonucleotides using different combinations of the phosphoramidites of 2'-deoxyadenosine (dA), 2'-deoxyguanosine (dG), 2'-deoxycytidine (dC), and 2'-deoxythymidine (dT) separated by the cleavable linker moiety of Formula (1) built up sequentially in a 3' to 5' direction from the 3' hydroxy of deoxyribose on a solid support according to the above method described by M. J. Gait. After synthesis the sequence may be represented by:

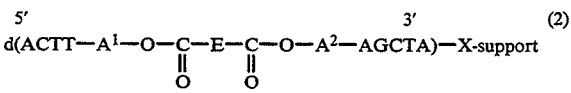

wherein X is a cleavable link.

After cleaving the linker moiety

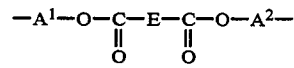

and the link X by which the first oligonucleotide is attached to the solid support two oligonucleotides result:

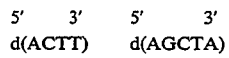

Thus two oligonucleotides have been synthesised on a single solid support.

It is preferred that the cleavable linker moiety connects the first and second oligonucleotides through a 3' and a 5' oxygen, more preferably through a phosphate, phosphite, phosphate ester, phosphite ester or H-phosphonate ester, one on each oligonucleotide.

The identity of the first cleavable link is not believed to be critical, it is preferably base labile, and may be for example any of the cleavable links used in automated oligonucleotide synthesisers, such as a link which contains a base labile ester group.

Organic residues of the cleaved linker moiety, such as hydrocarbon chains, preferably do not remain attached to the oligonucleotides after cleavage step (iv) to avoid any adverse affects on the properties of the oligonucleotides which such residues can have.

The first aspect of the invention includes repetition of steps (ii) and (iii) any desired number of times, for example 1 to 100 times, or preferably 1 to 5 times, to produce further oligonucleotides which are each connected through a cleavable linker moiety. As will be appreciated, when steps (ii) and (iii) are repeated the further oligonucleotides are formed on the cleavable linker moiety attached to the previously formed oligonucleotide and may be the same as or different to the previously formed oligonucleotides.

The cleavable linker moiety or moieties may be cleaved by base hydrolysis to give a mixture of individual oligonucleotides which may, if required, be purified and separated. Any suitable base may be used, for example, aqueous ammonia, methylamine.

In this specification the term "oligonucleotide" includes an oligodeoxyribonucleotide, an oligoribonucleotide and analogues thereof (for example those which bear protecting groups), including those with methyl-phosphonate and phosphorothioate or phosphorodithioate diester backbones, and oligonucleotides with oligodeoxyribonucleotides, especially the 2'-oligodeoxyribonucleotides being more usually synthesised by the method of the invention. The preferred oligonucleotides are oligodeoxyribonucleotides, are essentially single stranded, and are preferably from at least two, more preferably at least 5, especially from 10 to 200 bases long.

To users of DNA synthesisers the method of the invention gives the advantage of more effective use of the apparatus and subsequently reducing the cost of production and purification of oligonucleotides.

Thus with the present invention, the DNA synthesiser can produce two or more oligonucleotides (which may be the same or different) on any one of its columns without being re-programmed between each oligonucleotide. Thus when synthesis of one oligonucleotide is completed at a time outside the working day the synthesiser can go on to produce another without any intervention by an operative. This can significantly increase the productivity of such apparatus.

The method of the invention is particularly useful for the synthesis of primers for the Polymerase Chain Reaction (PCR) technique. At present a large proportion of oligonucleotides synthesised are for this purpose. Such primers are typically required in pairs and the method of the invention is convenient since it allows production of oligonucleotides in pairs. This is particularly an advantage when using single column synthesisers and/or for heavily used facilities for out-of hours working.

It is preferred that the precursors of the individual nucleotides are nucleoside phosphoramidites protected at the 5' oxygen atom and optionally are base protected. Methods of protecting nucleoside bases are known in the art, for example by a protecting group which is removable by treatment with mild acid or alkali. Adenine and cytosine may be protected by an optionally substituted N-benzoyl group and Guanine by an N-isobutyryl group. Thymine and uracil generally do not require protection. Adenine and guanine may also be protected by a dimethylformamide or phenoxyacetyl group, and cytosine by an isobutyryl group. The protecting groups are preferably removed after separation of the protected oligonucleotide from the support. Cleavage of the linker moiety may be effected before, during or after the removal of the protecting groups depending upon the chemistry employed. It is preferred that the protecting groups are removable by treatment with aqueous base, particularly concentrated ammonia solution or methylamine. In a preferred embodiment of the invention the cleavable linker moiety is cleavable under basic or alkaline conditions so that protecting group removal and cleavage of linker moieties can be effected in one step. Typical basic conditions employed, are to mix the protected oligonucleotide with base, for example, concentrated aqueous ammonia, methylamine or a mixture of both, or for example, methanolic sodium hydroxide. The reaction may be carried out, for example at a temperature of room temperature (20° C.) to 100° C., more preferably from 50° to 90° C., especially around 55° to 60° C. The reaction is typically carried out over a period of 48 hours, more particularly over a period up to 24 hours, especially from about 5 to 24 hours. It is preferred that a linker moiety is chosen such that cleavage is completed under these conditions.

Other bases, preferably volatile bases may be employed to effect cleavage. These may conveniently be organic amines in water, for example piperidine, diethylamine, or triethylamine, preferably at a concentration from 10-70%.

As examples of precursors of individual nucleotides suitable for use in the method there may be mentioned the 2-cyanoethyl-N,N-diisopropylaminophosphoramidites of 5'-dimethoxytrityl-N-4-benzoyl-2'-deoxycytidine, 5'-dimethoxytrityl-N-2-isobutyryl-2'-deoxyguanosine, 5'-dimethoxytrityl-N-6-benzoyl-2'-deoxyadenosine, and 5'dimethoxytritylthymidine.

For the synthesis of oligoribonucleotides precursors are, for example, the same as for oligodeoxyribonucleotides except that on the 2' position of the ribose there is a protected hydroxyl group, for example a tertiary butyl dimethyl silyloxy group or 2'—O—Fpmp phosphoramidites from Cruachem Ltd.

There is an increasing interest in the use of oligonucleotides having a 5' phosphate group (see e.g. Higuchi & Ockman (1989), Nucl. Acid Res. 17(14), p5865). Therefore a synthetic method that gives rise to an oligonucleotide having a 5' phosphate group is of value.

Thus, in a further aspect the method of the present invention step (iv) yields desired oligonucleotides each having a group selected from hydroxy and phosphate at the 3' and 5' position.

The cleavable linker moiety of Formula (1) may be attached to the first oligonucleotide using a reagent of Formula (3) in place of a precursor of an individual nucleotide in a manner analogous to conventional oligonucleotide synthesis.

Accordingly the present invention provides a compound of Formula (3):

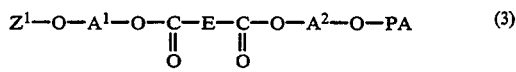 (3)

wherein $A^1$, $A^2$ and E are as hereinbefore defined; $Z^1$ is an acid labile protecting group; and —O—PA is a phosphoramidite group, a phosphate ester group or a H-phosphonate group.

Suitable acid labile protecting groups represented by $Z^1$ will be apparent to those skilled in the art and include those discussed in 'Protective Groups in Organic Synthesis' by T. W. Greene, Wiley Interscience. Examples of such protecting groups include methoxytrityl (preferably for oligoribonucleotide synthesis only), dimethoxytrityl, pixyl, isobutyloxycarbonyl, t-butyl dimethylsilyl and like protecting groups. Preferably, $Z^1$ is dimethoxytrityl.

E is preferably an organic spacer group having a length of 2 to 15, more preferably 2 to 6 carbon atoms. E is preferably an alkyl, alkenyl, aryl or aralkyl spacer group, optionally interrupted by an ether, thioether, amino or amido group. Preferred groups represented by E are optionally substituted phenylene, $C_{2-6}$-alkylene, more preferably —CH$_2$CH$_2$—.

$R^1$ and $R^2$ are preferably each independently H; straight or branched chain $C_{1-6}$-alkyl, especially methyl, ethyl, propyl, butyl or tertiary butyl; or $C_{1-6}$-alkoxy, especially methoxy, ethoxy, propoxy and butoxy, particularly methoxy; halogen, cyano, nitro, phenoxy, optionally protected hydroxy; optionally protected oxycarbonyl; or optionally protected NH$_2$.

Y is preferably CH$_2$, CH$_2$CH$_2$, NH or O, more preferably CH$_2$, CH$_2$CH$_2$ or O, especially O.

Each $R^3$ independently is preferably $C_{1-6}$-alkyl, especially methyl, ethyl, propyl or butyl or, more preferably, H. Optional substituents are as defined for $R^1$ and $R^2$.

As examples of groups represented by formula (b) there may be mentioned —*CH$_2$CH$_2$—SO$_2$—CH$_2$—CH$_2$— and —*CHCH$_3$—CH$_2$—SO$_2$—CH$_2$—CH$_2$—.

As will be understood, when —O—PA is a H-phosphonate or a phosphoramidite these are oxidised to respectively a phosphate diester or phosphate tri-ester groups during operation of the method, for example using aqueous iodine or peroxide. In the case of H-phosphonate the oxidation is preferably performed after step (iii) and before step (iv), whilst in the case of phosphoramidite it is preferably performed during step (i) and step (iii).

As examples of phosphate ester groups and H-phosphonate groups there may be mentioned groups which, in the free acid form, are respectively of formula:

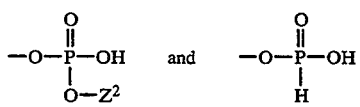

wherein $Z^2$ is a protecting group, preferably a base labile protecting group, for example 2-chlorophenyl or 2,4-dichlorophenyl.

Preferably, —O—PA is a phosphoramidite of general structure:

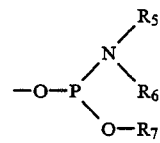

wherein $R_5$ and $R_6$ are each independently optionally substituted alkyl, especially $C_{1-4}$-alkyl; optionally substituted aralkyl, especially optionally substituted benzyl; cycloalkyl and cycloalkylalkyl containing up to ten carbon atoms, such as cyclopentyl or cyclohexyl; or $R_5$ and $R_6$ taken together with the nitrogen atom to which they are attached form an optionally substituted pyrollidine or piperidine ring or $R_5$ and $R_6$ when taken together with the nitrogen atom to which they are attached form a saturated nitrogen heterocycle which optionally includes one or more additional hetero atom from the group consisting of nitrogen, oxygen and sulphur. $R_5$ and $R_6$ are preferably iso-propyl.

$R_7$ represents a hydrogen atom or a protecting group, for example a phosphate protecting group. As examples of phosphate protecting groups there may be mentioned optionally substituted alkyl groups, for example methyl, 2-cyanoethyl, 2-chlorophenyl, 2,2,2-trihalo-1,1-dimethyl ethyl, 5-chloroquin-8-yl, 2-methylthioethyl and 2-phenylthioethyl groups in which the phenyl ring is optionally substituted, for example by a group selected from halogen, e.g. chlorine, or NO$_2$. Preferably $R_7$ is methyl or, more preferably, 2-cyanoethyl.

As will be appreciated by the skilled person the compounds of the present invention can exist in either the cis or trans form. However, the trans form of the compounds demonstrate a slower rate of cleavage and therefore result in oligonucleotides bearing terminal organic phosphate groups which may find applications in situations where the termini are required to be blocked.

The compounds of Formula (3) are suitable reagents for attaching a cleavable linker moiety of formula

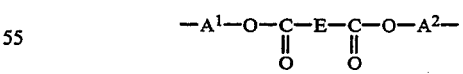

between a first and second oligonucleotide as described by the method of the invention. Under suitable conditions, for example treatment with concentrated ammonium hydroxide, the compounds cleave to give the desired oligonucleotides free from any organic residue of the compound of Formula (3). This is of particular value where oligonucleotides are desired with free or phosphated 3' or 5' termini.

The utility of compounds of Formula (3) can be illustrated by reference to the preparation of the sequence of Formula (2) as discussed above. For example, when $A^2$ is of Formula (a) the oligonucleotide of formula d(AGCTA) results having a 5' —OH group, and when $A^2$ is of Formula (b) d(AGCTA) results having a 5'-phosphate group. Accordingly, by appropriate selection of $A^2$ in a compound of Formula (3) from (a) and (b) the method of the invention provides the great benefit of enabling one to select whether the first, second, and subsequent oligonucleotides prepared according to the method of the invention have a hydroxy group at the 3' position and a hydroxy or phosphate group at the 5' position.

Compounds of Formula (3) wherein —O—PA is a phosphoramidite may be prepared by reacting a compound of the formula

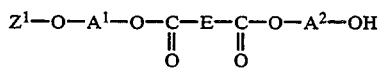

with a compound of formula $X^1$—PA in $CH_2Cl_2$ using di(N-isopropyl)ethylamine as base. PA is preferably a phosphoramidite as defined above for —O—PA except that —O— is absent, and $Z^1$, $A^1$, E and $A^2$ are as hereinbefore defined, and $X^1$ is a leaving group, for example Cl or Br.

When —O—PA in Formula (3) is a phosphate ester group as hereinbefore defined the compound of Formula (3) may be prepared by reaction of a compound of formula

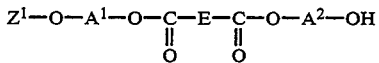

with the triazolide of the corresponding free phosphate ester using a method analogous to that described in the above book by M. J. Gait.

When —O—PA in Formula (3) is a H-phosphonate group as hereinbefore defined the compound of Formula (3) may be prepared by reaction in a compound of formula

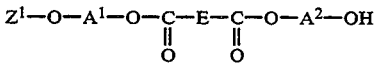

with $PCl_3$ in the presence of 1,2,4-triazole using a method analogous to that described by B. C. Froehler et al, Nucleic Acid Research, (1986), 14, 5399–5407.

The compound of formula

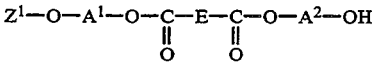

may be prepared, for example, by reaction of a compound of formula

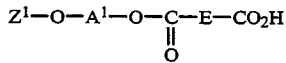

with a compound of formula HO—$A^2$—OH, preferably in an aprotic solvent using a suitable condensing agent such as the aforementioned DCCI or 1-(3-Dimethylaminopropyl)-3-ethylcarbodiimide.

The compound of formula

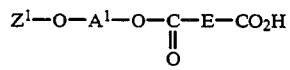

may be prepared by the reaction of the compound of formula $Z^1$—O—$A^1$—OH with an activated form of the compound of formula $HO_2C$—E—$CO_2H$, preferably in an aprotic solvent in the presence of a molar equivalent of base. The dicarboxylic acid may be activated to attack by the hydroxyl group by being present as the acid anhydride, the acid chloride or some other suitable derivative, or the reaction may be mediated by the presence of a coupling agent as described above.

The compound of formula $Z^1$—O—$A^1$—OH may be prepared by the reaction of the compound of formula HO—$A^1$—OH with $Z^1$—Cl (or some other suitably activated form of $Z^1$) in an anhydrous aprotic solvent in the presence of a molar equivalent of base.

When $A^1$ is of Formula (a) shown above the compound of formula $Z^1$—O—$A^1$—OH is preferably prepared by debenzoylation of a compound of formula $Z^1$—O—$A^1$—O—CO—Ph in methanol using methylamine. The compound of formula $Z^1$—O—$A^1$—O—CO—Ph may be prepared by reaction of compound of formula HO—$A^1$—O—CO—Ph with $Z^1$—$X^1$, wherein $X^1$ is a leaving group, for example Cl.

In the above processes for the preparation of the compound of Formula (3), and precursors thereof, $Z^1$, $A^1$, E, $A^2$, O, PA and $Z^2$ are as hereinbefore defined and DCCI is 1,3-dicylohexylcarbodiimide.

According to a further aspect of the invention there is provided a compound comprising two or more oligonucleotides linked, preferably by 3' and 5' oxygen atoms, by a group or groups containing a cleavable linker moiety of formula

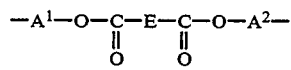

wherein $A^1$, E and $A^2$ are as hereinbefore defined. It is preferred that the cleavable linker moiety of formula

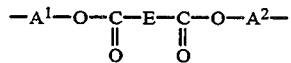

is connected to each oligonucleotide via a H-phosphonate, phosphate, phosphite, phosphate ester or phosphite ester linkage. It is preferred that one of the oligonucleotides is connected to a support.

H-phosphonate linkages are of formula —HP(=O)—, preferred phosphate ester linkages are of formula —P(=O)—$OR_6$— and preferred phosphite linkages are of formula —P(—$OR_6$)— wherein $R_6$ is as hereinbefore defined.

The invention is illustrated by the following non-limiting examples:

EXAMPLE 1

Preparation of Reagent A1

This was synthesised using the preparation numbered 1 to 4 described below. DMT is 4,4'dimethoxytrityl.

Step 1—Preparation of:

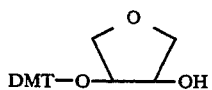

To a solution of 1,4-anhydroerythritol (10.4 g, 100 mmol) in dry pyridine (100 ml) at 0° C., benzoyl chloride (14 g, 100 mmol) was added dropwise with stirring. When addition was complete, the solution was allowed to warm to room temperature and stirring was maintained for a further two hours. To this solution was added 4,4'-dimethoxytrityl chloride (37.4 g, 110 mmol) and 4-(N,N-dimethylamino)pyridine (100 mg) and the mixture was stirred at room temperature for 16 hours. The solvent was removed by rotary evaporation and the residue redissolved in dichloromethane and washed three times with saturated sodium bicarbonate solution. The dichloromethane solution was dried by the addition of anhydrous sodium sulphate and filtered. The filtrate was evaporated to a gum and redissolved in methanol saturated with methylamine. The resultant solution was incubated at room temperature until no starting material could be detected by TLC. The solvent was removed by rotary evaporation, and the residue redissolved in the minimum volume of dichloromethane/methanol (9/1) and loaded on a silica chromatography column. Elution with the same solvent gave the title compound as a white foam (22 g, 54%).

$^1$H NMR: (δ, CDCl$_3$): 3.35, 1H, multiplet, CHOH; 3.5, 2H, doublet, —CH$_2$—; 3.75, 8H, complex multiplet, 2× —OCH$_3$ and —CH$_2$—; 4.2, 1H, complex multiplet, DMT—OCH; 6.9, 4H, complex multiplet, aromatics; 7.25–7.5, 9H, complex multiplet, aromatics.

Step 2—Preparation of:

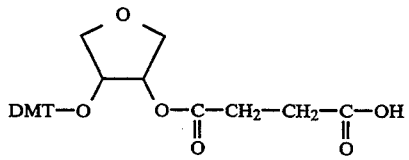

The product from step 1 (10 g, 24.6 mmol) was dissolved in dry pyridine (150 ml) and succinic anhydride (10 g, 100 mmol) was added. When dissolution was complete, 4-(N,N-dimethylamino)pyridine (500 mg) was added and the solution was stirred at room temperature overnight. The solvent was evaporated under reduced pressure and residual pyridine removed by repeated co-evaporation with toluene. The residue was redissolved in dichloromethane (500 ml) and washed three times with ice cold 10% citric acid solution. The organic layer was separated, dried (sodium sulphate) filtered and evaporated to a gum which was redissolved in the minimum volume of dichloromethane/methanol (9/1) and loaded on a silica chromatography column. Elution with the same solvent gave the title compound as a white foam (9.7 g, 78%).

$^1$H NMR: (δ, CDCl$_3$): 2.75, 4H, multiplet, 2× COCH$_2$; 2.9 and 3.2, 2H, two pseudo triplets, —CH$_2$—; 3.75, 8H, complex multiplet, 2× —OCH$_3$ and —CH$_2$—; 4.2, 1H, complex multiplet, DMT—OCH; 5.0, 1H, multiplet, CHOCO; 6.9, 4H, complex multiplet, aromatics; 7.25–7.5, 9H, complex multiplet, aromatics.

Step 3—Preparation of:

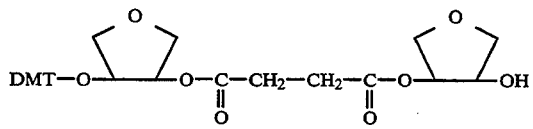

The product from step 2 (10 g, 19.5 mmol) was dissolved in dry pyridine (200 ml) containing 1,4-anhydroerythritol (10.4 g, 100 mmol). To this solution was added 1-(3-dimethylaminopropyl)-3-ethyl carbodiimide hydrochloride (Aldrich, 3.75 g, 19.5 mmol). The solution was stirred at room temperature overnight when TLC in dichloromethane:methanol (19:1) showed there to be no starting material present. The solvent was removed under reduced pressure and residual pyridine removed by repeated co-evaporation with toluene. The residue was redissolved in ethyl acetate and washed three times with saturated sodium bicarbonate solution and once with water. The organic layer was separated, dried (sodium sulphate), filtered and evaporated under reduced pressure to give a gum which was redissolved in the minimum volume of dichloromethane:methanol (19:1) and loaded on a silica chromatography column. Elution with the same solvent gave the title compound as a colourless gum (9.5 g, 79%).

$^1$H NMR: (δ, CDCl$_3$): 2.75–2.9, 5H, multiplet, 2× COCH$_2$+—OH; 3.2, 2H, multiplet, —CH$_2$—; 3.65–3.85, 10H, complex multiplet, 2× —OCH$_3$ and 2× —CH$_2$—; 3.9–4.1, 2H, multiplet, —CH$_2$—; 4.2, 1H, complex multiplet, DMT—O—CH; 4.4, 1H, multiplet, CHOH; 5.0 and 5.1, 2H, two multiplets, 2× CHOCO; 6.9, 4H, complex multiplet, aromatics; 7.25–7.5, 9H, complex multiplet, aromatics.

Step 4—Preparation of Reagent A1

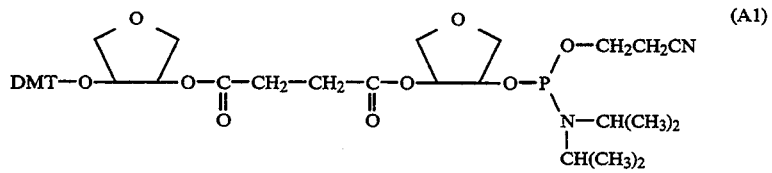

(A1)

The product from step 3 (2 g, 3.3 mmol) was dissolved in dry dichloromethane (50 ml) and the solution stirred under a stream of dry argon. To this solution was added dry diisopropylethylamine (2.7 ml, 16 mmol) and 2-cyanoethyl-N,N-diisopropylaminochlorophosphine (1.05 ml, 4.72 mmol). The solution was stirred at room temperature under a stream of dry argon for 30 minutes when TLC in dichloromethane:triethylamine (19:1) showed there to be no starting material present. The reaction was quenched by addition of dry methanol (5 ml) and the solution was diluted with ethyl acetate (200 ml). This solution was washed with three equal volumes of saturated sodium chloride solution, and one volume of water. The organic layer was separated, dried (sodium sulphate), filtered and evaporated under reduced pressure to a gum which was redissolved in the minimum volume of dichloromethane:triethylamine (19:1)

and loaded on a silica choromatography column. Elution with the same solvent gave the title reagent A1 as a colourless gum (1.8 g, 65%).

$^1$H NMR: (δ, CDCl$_3$): 1.1–1.3, 12H, multiplet, 4× CH$_3$—; 2.6, 2H, multiplet, CH$_2$CN; 2.8–3.2, 6H, multiplet, 2× COCH$_2$ and —CH$_2$—; 3.5–3.9, 14H, complex multiplet, 2× —OCH$_3$, 2× CH(CH$_3$), POCH$_2$—, 2× —CH$_2$—; 4.0–4.2, 3H, complex multiplet, —CH$_2$ and DMT—OCH; 4.5, 1H, multiplet, CH—O—P; 5.0, 1H, multiplet, CHOCO; 5.3, 1H, multiplet, CHOCO; 6.8, 4H, multiplet, aromatics; 7.2–7.5, 9H, complex multiplet, aromatics.

EXAMPLE 2

Preparation of Two Oligonucleotides on a Single Support

An oligonucleotide was formed on a solid support via a first (conventional) cleavable link using the protocol supplied with the Applied Biosystems 380B DNA synthesiser, using the 3'-(2-cyanoethyl)-N,N-diisopropylamminophosphoramidites of 5'-dimethoxytrityl-N$^4$-benzoyl-2'deoxycytidine, 5'-dimethoxytrityl-N$^2$-isobutyryl-2'deoxyguanosine, 5'-dimethoxytrityl-N$^6$-benzoyl-2'deoxyadenosine and 5'-dimethoxytritylthymidine (Cruachem) as the precursors of the individual nucleotides. A cleavable linker moiety was attached to the first oligonucleotide by means of reagent A1. Reagent A1 was dissolved in anhydrous acetonitrile to a concentration of 0.1M, and a bottle containing this solution was attached to one of the spare reagent ports on the DNA synthesiser. A column containing controlled pore glass or solid support bearing a 5'-protected nucleoside (in this case deoxyadenosine) connected by means of a (conventional) cleavable link (succinylglycylglycylaminopropyl, Cruachem) was attached to the synthesiser. The synthesiser was then programmed to synthesise the following sequence (SEQ ID NO:1):

(5') TTTTTTTTTT—L'—TCGA (3')

(whereby the cleavable linker moiety L' is introduced by means of reagent A1), using standard synthesis cycles employed on the Applied Biosystems 380B DNA synthesiser. The duration of the reaction steps and the volume of reagents used for coupling, oxidation, capping and detritylation were identical for each coupling, including that of reagent A1. The synthesiser was programmed to perform the conventional concentrated ammonia wash of the column to release the oligonucleotides into collection vials.

In this manner the synthesiser achieves the steps of a) forming a first oligonucleotide of sequence (5'-3') TCGA by succesive reaction of the nucleotide precursors with an oligonucleotide connected to the controlled pore glass support via the 3'—OH group and a (conventional) first cleavable link, b) attaching to the first oligonucleotide a cleavable linker moiety by means of reagent A1, and c) forming a second oligonucleotide on the cleavable linker moiety having the sequence (5'-3') TTTTTTTTTT, to give two oligonucleotides separated by a cleavable linker moiety and bound to a solid support by a cleavable link, as illustrated by the formula:

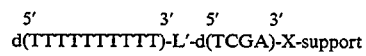

wherein —L'— is a cleavable linker of formula:

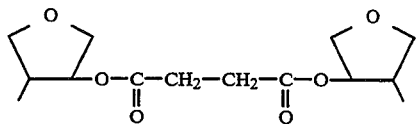

attached to the 5' and 3' oxygen of the first and second oligonucleotides respectively by a group of formula —P(O)(OCH$_2$CH$_2$CN)—O—, and X is a first cleavable link contained in the succinylglycylglycylaminopropyl spacer. The synthesiser also performs the cleavage of the first cleavable link X by the ammonium treatment as in step d) in the method of the invention.

To the vial containing the eluted oligonucleotide in the ammonium solution was added 1 ml of 40% aqueous methylamine, and the vial was then incubated at 55° C. for 16 hours and evaporated to dryness under reduced pressure. The residue was redissolved in 1 ml of water.

Five other oligonucleotides were also synthesised by conventional procedures as described above but omitting the treatment with methylamine. These were designed to represent control molecules to be used in the analysis of products generated by the methylamine treatment above. These oligonucleotides had the following sequences:

1) (5') TTTTTTTTTT (3')
2) (5') TCGA (3')
3) (5') PO$_4{}^{2-}$ TTTTTTTTTT (3')
4) (5') PO$_4{}^{2-}$ TCGA (3')
5) (5') TTTTTTTTTTTTCGA (3') (SEQ ID NO:2)

Thus, oligonucleotides 1) and 2) are of identical length and sequence to the products expected from cleavage of the oligonucleotide containing the cleavable link, and oligonucleotides 3, 4 and 5 are representative of the products expected from partial cleavage of the oligonucleotide containing the cleavable link.

The mixture of oligonucleotides produced in step d) described above was analysed by ion-exchange HPLC on a Pharmacia Mono-Q column using a linear gradient from 0–25% buffer B in buffer A over 35 minutes where buffer A was 50 mM Tris-chloride (pH 7.5) and buffer B was 50 mM Tris-chloride/800 mM sodium chloride (pH 7.5).

Under these conditions, control oligonucleotide 1) had a retention time of 29 minutes, control sequence 2) had a retention time of 9 minutes, control sequence 3) had a retention time of 32 minutes, control sequence 4) had a retention time of 13 minutes and control sequence 5) had a retention time of 39 minutes.

The HPLC profile of the mixture of oligonucleotides produced in step d) above showed only peaks corresponding to the presence of oligonucleotides 1 and 2, thus confirming that complete scission of the cleavable link had occurred, generating the desired products.

EXAMPLE 3

Preparation of Reagent A2

This was synthesised using the preparations numbered 1 to 2 below. DMT is 4,4'-dimethoxytrityl.

Step 1: Preparation of:

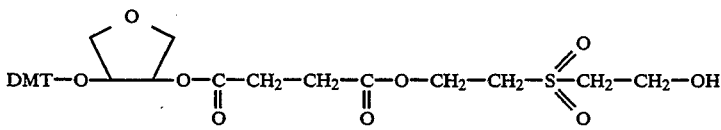

The product from Example 1), step 2) (10 g, 19.5 mmol) was dissolved in dry pyridine (200 ml) containing 2,2'-sulfonyldiethanol (15 g, dried by azeotropic distillation with toluene below 45° C.). To this solution was added 1-(3-dimethylaminopropyl)-3-ethylcarbodiimide hydrochloride (3.75 g, 19.5 mmol) and the whole was stirred at room temperature overnight. The solvent was removed under reduced pressure and residual pyridine was removed by repeated co-evaporation with toluene. The gummy residue was redissolved in ethyl acetate (300 ml) and washed with saturated sodium bicarbonate (3×200 ml) and water (200 ml). The organic layer was separated, dried (MgSO$_4$), filtered and evaporated to give a gum which was redissolved in the minimum volume of dichloromethane:methanol (19:1) and applied to a silica column. Elution with the same solvent gave the title compound as a colourless gum (8.2 g, 66.3%).

$^1$H NMR δ (CDCl$_3$): 2.75 (4H, m, 2× COCH$_2$); 2.9–3.3 (4H, m, —CH$_2$— and —CH$_2$OH); 3.45 (2H, t, CH$_2$SO$_2$); 3.7–3.9 (8H, m, 2× —OCH$_3$ and —CH$_2$—); 4.0 (2H, t, CH$_2$SO$_2$); 4.2 (1H, m, DMT—OCH); 4.55 (2H, t, —CH$_2$OCO); 5.0 (1H, m, CHOCO); 6.9 (4H, m, aromatics); 7.25–7.5 (9H, m, aromatics).

Step 2: Preparation of reagent A2:

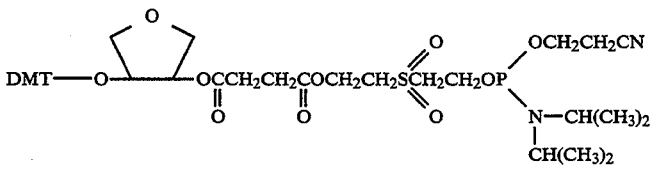

The product from Step 1) (4 g, 6.2 mmol) was dissolved in dry dichloromethane (50 ml) containing dry diisopropylethylamine (4.4 ml, 25 mmol) and the solution was stirred under a stream of dry argon while 2-cyanoethyl-N,N-diisopropylaminochlorophosphine (1.67 ml, 7.44 mmol) was added dropwise. The solution was stirred under argon at room temperature for a further thirty minutes when TLC in dichloromethane:triethylamine (19:1) showed there to be no starting material present. The reaction was quenched by the addition of dry methanol (5 ml), and the solution was diluted with ethyl acetate (200 ml). This solution was washed with brine (3×200 ml) and water (200 ml). The organic layer was separated, dried (MgSO$_4$), filtered and evaporated to a gum which was redissolved in the minimum volume of dichloromethane:hexane:triethylamine (42:55:3) and applied to a silica column. Elution with the same solvent followed by elution with dichloromethane:triethylamine (19:1) gave the title compound as a colourless glass (3.8 g, 72.5%)

$^1$H NMR: δ (CDCl$_3$): 1.15–1.3 (14H, m, 2× CH(CH$_3$)$_2$); 2.6–2.75 (6H, m, 2× COCH$_2$ and CH$_2$CN); 3.3 (2H, m, —CH$_2$—); 3.45–3.6 (6H, m, CH$_2$SO$_2$ and 2× CH$_2$OP); 3.7–4.0 (10H, m, 2× —OCH$_3$, —CH$_2$— and —CH$_2$SO$_2$); 4.2 (1H, m, DMT—OCH); 4.5 (2H, m, —CH$_2$OCO); 5.0 (1H, m, CHOCO); 6.9 (4H, m, aromatics); 7.2–7.5 (9H, m, aromatics).

EXAMPLE 4

The method of Example 2) was repeated to synthesise two oligodeoxyribonucleotides bound to a solid support, except that Reagent A2 was used, dissolved in anhydrous acetonitrile to a concentration of 0.1M, in place of Reagent A1.

The two oligonucleotides bound to a solid support by a cleavable link are illustrated by the formula given in Example 2), wherein —L'— is a cleavable linker of formula:

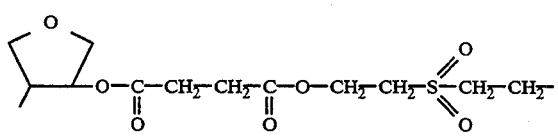

The two oligonucleotides found after step d) in the method of the invention were found to be identical to oligonucleotides 1) and 4) described in Example 2), demonstrating scission of the cleavable link and phosphorylation of the 5'-hydroxyl of the oligonucleotide formed in step a) in the method of the invention.

EXAMPLE 5

Step 1—Preparation of Reagent A3

This was synthesised using the preparations numbered a) to f) below. DMT is 4,4'-dimethoxytrityl.

a) Preparation of r-3,Cis-4-dihydroxy-cis plus trans-2,-trans-5-dimethoxytetrahydrofuran

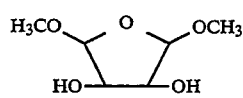

2,5-Dihydro-2,5-dimethoxyfuran (50 g; Aldrich, cis/trans mixture) was dissolved in tetrahydrofuran (500 ml) in a 5 liter, three-necked flask fitted with a mechanical stirrer. The contents of the flask were cooled to −5° C., and a solution of potassium permanganate (61.9 g) in water (2250 ml) was added dropwise with vigorous stirring at such a rate as to keep the temperature of the flask contents between 4° and 6° C. This addition took 80 minutes. The reaction mixture was then left stirring and allowed to warm to room temperature over 15 hours. The precipitated manganese dioxide was filtered off through Celite and washed with THF (200 ml). The clear colourless filtrate was evaporated and the residue was shaken vigorously with ethyl acetate (200 ml) until no material adhered to the flask wall. The fine precipitate of KOH was filtered off on a glass sinter and washed with ethyl acetate. The filtrate was rotary evaporated to give the title compound as a golden syrup (24.4 g, 38.6%). The compound was mainly the meso product (80%) contaminated with the dl compound (20%).

¹³C-NMR:

| meso product | CH₃O | 55.462 ppm |
| --- | --- | --- |
| | CHOH | 75.303 ppm |
| | CHOCH₃ | 109.606 ppm |
| dl product | CH₃O | 56.451 ppm |
| | CHOH | 70.654 and 73.604 ppm |
| | CHOCH₃ | 103.155 and 108.257 ppm | b) Preparation of

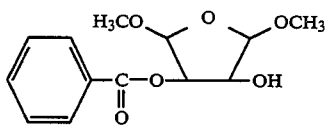

The product from step a) above (1.7 g) was dissolved in dry pyridine (10 ml) and 4-N,N-dimethylaminopyridine (DMAP) (100 mg) was added. The mixture was swirled to dissolve the solid and benzoyl chloride (1.2 ml) was added. The mixture was then left to stand at 20° C. for 16 hours. The mixture was rotary evaporated, and residual pyridine was removed by repeated co-evaporation with toluene. The residual oil was partitioned between ethyl acetate and 1M HCl (40 ml of each). The organic layer was washed in succession with water, 1M NaHCO₃, and saturated brine (40 ml of each), dried over magnesium sulphate, filtered and rotary evaporated. The residual oil was redissolved in dichloromethane/methanol (19/1) and applied to a silica column. Elution with the same solvent gave the desired product as a white solid (1.11 g, 38%)

¹³C-NMR:
CH₃O: 55.680 and 55.951 ppm
CHOH and CHOCO: 75.016 and 77.973 ppm
CHOCH₃: 107.136 and 109.899 ppm
C₆H₅: 128.576, 129.300, 129.957 and 133.952 ppm
CO: 166.076 ppm c) Preparation of

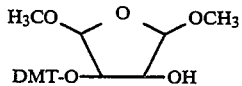

The product from step b) above (2.47 g), 4,4'-dimethoxytrityl chloride (3.12 g) and DMAP (0.15 g) were stirred in dry pyridine (20 ml) at room temperature for 16 hours. The solvent was removed by rotary evaporation and residual pyridine was removed by repeated co-evaporation with toluene. The residue was partitioned between ethyl acetate and water (50 ml of each) and the organic layer was washed with 1M sodium bicarbonate, then saturated brine (20 ml of each), dried over magnesium sulphate, filtered and rotary evaporated to an oil which was dissolved in a solution of methylamine in methanol (120 ml, 7.5M) and incubated at room temperature for 24 hours. The solution was filtered and the filtrate was evaporated to an oil which was redissolved in the minimum volume of petroleum (b.p. 60°–80° C.)/ethyl acetate (3/2) and applied to a silica column. Elution with the same solvent gave the desired product (2.3 g) as a white foam which was used directly in the next step without further characterisation.

d) Preparation of Reagent A1

The product from step c) above (2.28 g) was dissolved in dry pyridine (20 ml) and succinic anhydride (0.55 g) and DMAP (0.4 g) were added. The mixture was swirled to dissolve the solids and then left at room temperature for 16 hours. The solvent was removed by rotary evaporation and residual pyridine was removed by repeated co-evaporation with toluene. The residue was partitioned between ethyl acetate and 10% (w/v) citric acid (50 ml of each). The organic layer was washed with water then saturated brine (50 ml of each), dried over magnesium sulphate, filtered and rotary evaporated to an oil which was redissolved in the minimum volume of dichloromethane/methanol (19/1) and applied to a silica column. Elution with the same solvent gave the title compound as a colourless glass (1.98 g, 71.4%).

¹³C-NMR:
CH₂ groups of OCCH₂CH₂CO: 28.790 ppm and 28.939 ppm
CH₃OAr: 54.988 ppm
CH₃OCH×2: 55.251 ppm
CH₃OAr: 56.039 ppm
CHODMT and CHOCO: 75.518 ppm and 76.424 ppm
quat C of DMT: 106.572 ppm and 87.194 ppm
CHOCH₃: 106.572 and 109.102 ppm
ArCH: 113.245 ppm, 127.821 ppm, 128.337 ppm, 129.160 ppm, 130.250 ppm and 130.280 ppm
Ar quat C: 139.893 ppm, 136.035 ppm, 144.855 ppm and 158.859 ppm
COO: 170.879 ppm
COO: 177.540 ppm e) Preparation of:

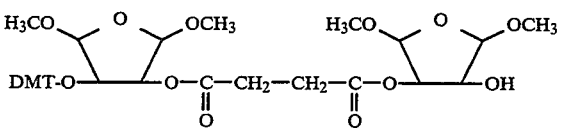

The product from step d) (1.881 g) was dissolved in dry dichloromethane (5 ml) and N,N'-dicyclohexylcarbodiimide (0.384 g, 0.5 meq) was added. The solid was dissolved by swirling the flask, which was then left at 20° C. for one hour. Dicyclohexylurea was filtered off and washed with dichloromethane (3×2 ml). The filtrate and washings were combined and rotary evaporated. To this was added a solution of the product from step 1) (0.708 g, 1.27 meq) in dry pyridine (6 ml). When dissolution was complete, the flask was left at 20° C. for thirty nine hours, and then rotary evaporated. Residual pyridine was removed by repeated co-evaporation with toluene. The residual oil was dissolved in the minimum volume of dichloromethane:methanol (96:4), and applied to a silica column. Elution with the same solvent gave the title compound as a yellow foam (0.764 g, 63.4%)

¹H NMR δ (CDCl₃): 2.6–2.8 (4H, m, 2× COCH₂); 3.25–3.5 (12H, 4s, 4×—OCH₃); 3.8 (6H, s, 2× ArOCH₃); 4.0 (1H, DMT—OCH); 4.35 (1H, m, CHOCH₃); 4.45 (1H, m, CHOCH₃); 4.8 (1H, m, CHOH); 5.0 (2H, m, 2× CHOCO); 5.15 (2H, m, 2×

CHOCH₃); 6.9 (4H, m, aromatics); 7.1-7.55 (9H, m, aromatics).

f) Preparation of Reagent A3:

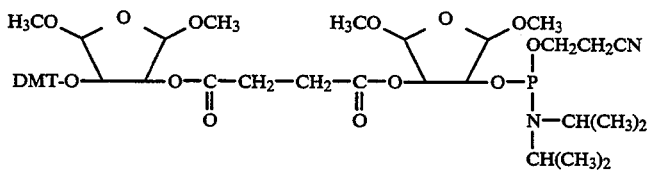

The product from Step e) (0.5 g, 0.702 mmol) was dissolved in dry dichloromethane (15 ml) containing dry diisopropylethylamine (0.495 ml, 2.81 mmol) and the solution was stirred under a stream of dry argon while 2-cyanoethyl-N,N-diisopropylaminochlorophosphine (0.189 ml, 0.843 mmol) was added dropwise. The solution was stirred under argon at room temperature for a further thirty minutes when TLC in dichloromethane:triethylamine (19:1) showed there to be no starting material present. The reaction was quenched by the addition of dry methanol (5 ml), and the solution was diluted with ethyl acetate (200 ml). This solution was washed with brine (3×200 ml) and water (200 ml). The organic layer was separated, dried (MgSO₄), filtered and evaporated to a gum which was redissolved in the minimum volume of dichloromethane:hexane:triethylamine (42:55:3) and applied to a silica column. Elution with the same solvent followed by elution with dichloromethane:triethylamine (19:1) gave the title compound as a colourless glass (0.52 g, 81.3%)

¹H NMR δ (CDCl₃): 1.1-1.3 (14H, m, 2× C$\underline{H}$(CH₃)₂; 2.5 (2H, m, C$\underline{H}_2$CN); 2.6-2.8 (4H, m 2× COC$\underline{H}_2$); 3.2-3.6 (14H, m 4× —OC$\underline{H}_3$ and CH₂OP ); 3.8 (6H, s, 2× ArOC$\underline{H}_3$); 4.0 (1H, m, DMT—OC$\underline{H}$); 4.3 (1H, m, C$\underline{H}$OCH₃); 4.4-4.6 (2H, m, C$\underline{H}$OCH₃ and C$\underline{H}$OP); 5.0 (2H, m, 2× C$\underline{H}$OCO); 5.2 (2H, m, 2× C$\underline{H}$OCH₃); 6.9 (4H, m, aromatics); 7.1-7.5 (9H, m, aromatics).

EXAMPLE 6

The method of Example 2) was repeated to synthesise two oligodeoxyribonucleotides bound to a solid support, except that Reagent A3 was used, dissolved in anhydrous acetonitrile to a concentration of 0.1M, in place of Reagent A1.

The two oligonucleotides bound to a solid support by a cleavable link are illustrated by the formula given in Example 2), wherein —L'— is a cleavable linker of formula:

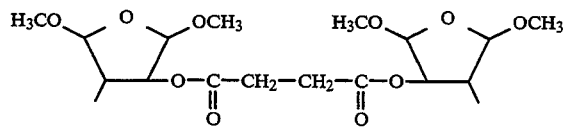

The two oligonucleotides found after step d) in the method of the invention were found to be identical to oligonucleotides 1) and 2) described in Example 2), demonstrating scission of the cleavable link and generation of the desired products.

---

We claim:

1. A method for the synthesis of a plurality of oligonucleotides comprising the steps of
   (i) forming a first oligonucleotide on a first cleavable link attached to a solid support;
   (ii) attaching to the first oligonucleotide a cleavable linker moiety;
   (iii) forming a second oligonucleotide on the cleavable linker moiety; and
   (iv) cleaving the first cleavable link and the cleavable linker moiety to give a plurality of oligonucleotides; wherein the cleavable linker moiety is of the Formula (1):

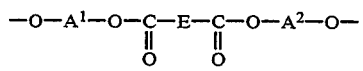

wherein one or both of $A^1$ and $A^2$ is a divalent group of the formula (a):

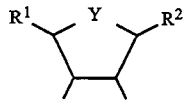

$R^1$ and $R^2$ are each independently H, optionally substituted alkyl, optionally substituted alkoxy, optionally substituted aryloxy, halogen, cyano, nitro, optionally protected hydroxy, optionally protected oxycarbonyl, optionally protected $NH_2$ or an electron withdrawing group; Y is $CH_2$, $CH_2CH_2$, NH, S or O; E is an organic spacer group; and any remaining group represented by $A^1$ or $A^2$ is of the formula (b):

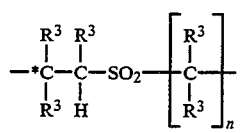

wherein n has a value of from 1 to 5; the carbon atom marked with an asterisk is attached to an oxygen atom shown in Formula (1); and each $R^3$ independently represents H or optionally substituted alkyl.

2. A method according to claim 1 wherein cleavage of the cleavable linker moiety results in a plurality of oligonucleotides each having at the 3' and 5' position a group selected from hydroxy and phosphate.

3. A method according to claim 1 or 2 wherein cleavage of the cleavable linker moiety results in a plurality of oligonucleotides each having a hydroxy at the 3' position.

4. A method according to claim 1 wherein steps (i) to (iii) are carried out using an automated oligonucleotide synthesizer and step (iv) is carried out under basic conditions at a temperature from 20° to 100° C. for up to 48 hours.

5. A method according to claim 1 wherein the cleavable linker moiety of formula (1) is derived from a compound of formula (3):

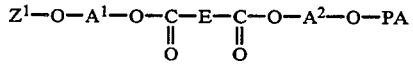

wherein one or both of $A^1$ and $A^2$ is a divalent group of the formula (a):

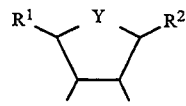

in which $R^1$ and $R^2$ are each independently H, optionally substituted alkyl, optionally substituted alkoxy, optionally substituted aryloxy, or an electron withdrawing group; Y is $CH_2$; $CH_2CH_2$, NH, S or O; E is an organic spacer group; and any remaining group represented by $A^1$ or $A^2$ is of the formula (b):

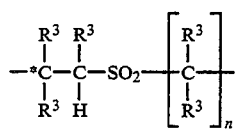

wherein: n has a value of from 1 to 5; the carbon atom marked with an asterisk is attached to an oxygen atom shown in Formula (3); and each $R^3$ independently represents H or optionally substituted alkyl; $Z^1$ is an acid labile protecting group; and —O—PA is a phosphoramidite group, a phosphate ester group or a H-phosphonate group.

6. A method according to claim 5 wherein $A^1$ and $A^2$ are both of formula (a).

7. A method according to claim 6 wherein $A^1$ is the group of formula (a) and $A^2$ is the group of formula (b).

8. A method according to claim 7 wherein Y is O or $CH_2$.

9. A method according to claim 8 wherein E is an alkyl, aryl or aralkyl spacer group, optionally interrupted by an ether, thioether, amino or amido group.

10. A method according to claim 9 wherein E is optionally substituted phenylene or $C_{2-6}$-alkylene.

11. A method according to claim 10 wherein $R^1$ and $R^2$ are each independently H, alkyl or alkoxy.

12. A method according to claim 11 wherein $R^3$ is independently $C_{1-4}$-alkyl or H.

13. A method according to claim 12 wherein $Z^1$ is dimethoxytrityl.

14. A method according to claim 13 wherein O—PA is a phosphoramidite of formula

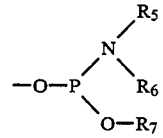

wherein $R_5$ and $R_6$ are each independently optionally subsituted alkyl, optionally substituted aralkyl, cycloalkyl and cycloalkylalkyl containing up to 10 carbon atoms, or taken togther with the nitrogen atom to which they are attached form an optionally substituted pyrrolidine or piperidine ring or $R_5$ and $R_6$ when taken together with the nitrogen atom to which they are attached form a saturated nitrogen heterocycle which optionally includes one or more additional hetero atom(s) from the group consisting of nitrogen, oxygen and sulphur; and $R_7$ represents a hydrogen or a protecting group.

15. A method according to claim 14 wherein the group of formula (a) is where Y is O and $R^1$ and $R^2$ are both either hydrogen or methoxy; and the group of formula (b) is —*CH$_2$CH$_2$—SO$_2$—CH$_2$—CH$_2$.

16. A method according to claim 15 wherein A$^1$ and and A$^2$ are both of formula (a), Y is O, R$^1$ and R$^2$ are both hydrogen or methoxy, E is —CH$_2$CH$_2$—, Z$^1$ is dimethoxytrityl, and O—PA is a phosphoramidite of formula

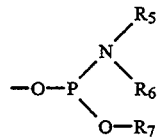

wherein R$_5$ and R$_6$ are each iso-propyl and R$_7$ is 2-cyanoethyl.

17. A method according to claim 16 wherein A$^1$ is of formula (a) in which Y is O and R$^1$ and R$^2$ are both hydrogen or methoxy and A$^2$ is —*CH$_2$CH$_2$—SO$_2$—CH$_2$—CH$_2$—, Z$^1$ is dimethoxytrityl, and O—PA is a phosphoramidite of formula

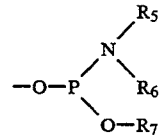

wherein R$^5$ and R$^6$ are both iso-propyl and R is 2-cyanoethyl.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TTTTTTTTTT      10

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

TTTTTTTTTT TTCGA      15